United States Patent
Minagawa (10) Patent No.: US 9,752,003 B2
(45) Date of Patent: *Sep. 5, 2017

(54) SURFACE-MODIFIED ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 812 days.

This patent is subject to a terminal disclaimer.

(21) Appl. No.: 14/077,829

(22) Filed: Nov. 12, 2013

(65) Prior Publication Data

US 2014/0155510 A1    Jun. 5, 2014

(30) Foreign Application Priority Data

Nov. 30, 2012   (JP) .................. 2012-262842

(51) Int. Cl.
*C08J 7/18*   (2006.01)
*C08J 3/28*   (2006.01)
(Continued)

(52) U.S. Cl.
CPC ............ *C08J 7/18* (2013.01); *A61L 29/042* (2013.01); *A61L 29/06* (2013.01); *A61L 29/08* (2013.01);
(Continued)

(58) Field of Classification Search
CPC .. A61M 5/178; A61M 25/00; A61M 25/0009; A61M 25/0045; A61M 3/00;
(Continued)

(56) References Cited

U.S. PATENT DOCUMENTS

| 3,418,066 A | 12/1968 | Caldwell et al. |
| 5,100,689 A | 3/1992 | Goldberg et al. |

(Continued)

FOREIGN PATENT DOCUMENTS

| CN | 101565489 A | 10/2009 |
| CN | 102382291 A | 3/2012 |

(Continued)

OTHER PUBLICATIONS

Allmér et al., "Surface Modification of Polymers. I. Vapour Phase Photografting with Acrylic Acid," Journal of Polymer Science: Part A: Polymer Chemistry, vol. 26, 1988, pp. 2099-2111.
(Continued)

*Primary Examiner* — Walter B Aughenbaugh
(74) *Attorney, Agent, or Firm* — Birch, Stewart, Kolasch & Birch, LLP (57) ABSTRACT

Provided are surface-modified elastic bodies (e.g. gasket for syringes) each obtained by a surface modification method for modifying a rubber vulcanizate or a thermoplastic elastomer, the method being capable of providing surfaces with excellent properties such as excellent sliding properties, excellent durability against repeated sliding motion, and excellent performance in preventing adsorption and aggregation of proteins, and allowing the surfaces to maintain the sealing properties, without using expensive self-lubricating plastics. The invention relates to surface-modified elastic bodies (e.g. gasket for syringes) at least partially having a surface modified by a surface modification method including: step 1 of forming polymerization initiation points on a surface of an object to be modified that includes a rubber vulcanizate or thermoplastic elastomer, and step 2 of radically polymerizing a monomer containing a C—N bond in a molecule thereof, starting from the polymerization initiation points, to grow polymer chains on the surface of the object.

13 Claims, 1 Drawing Sheet (51) Int. Cl.

| | | |
|---|---|---|
| *C08F 2/48* | (2006.01) | |
| *A61M 5/178* | (2006.01) | |
| *C08F 36/18* | (2006.01) | |
| *A61M 3/00* | (2006.01) | |
| *A61M 25/00* | (2006.01) | |
| *A61L 29/06* | (2006.01) | |
| *B05D 3/06* | (2006.01) | |
| *A61L 29/04* | (2006.01) | |
| *A61L 29/08* | (2006.01) | |
| *C08F 291/04* | (2006.01) | |
| *C08J 7/12* | (2006.01) | |
| *C08F 220/56* | (2006.01) | |
| *C08F 291/02* | (2006.01) | |
| *A61L 29/14* | (2006.01) | |
| *A61M 5/315* | (2006.01) | |

(52) U.S. Cl.
CPC ............ *A61L 29/085* (2013.01); *A61L 29/14* (2013.01); *A61M 3/00* (2013.01); *A61M 5/178* (2013.01); *A61M 25/00* (2013.01); *A61M 25/0009* (2013.01); *A61M 25/0045* (2013.01); *B05D 3/067* (2013.01); *C08F 2/48* (2013.01); *C08F 36/18* (2013.01); *C08F 220/56* (2013.01); *C08F 291/02* (2013.01); *C08F 291/04* (2013.01); *C08J 3/28* (2013.01); *C08J 7/12* (2013.01); *A61L 2400/18* (2013.01); *A61M 5/31513* (2013.01); *A61M 2025/0046* (2013.01); *A61M 2025/0056* (2013.01); *A61M 2025/0062* (2013.01); *C08J 2323/28* (2013.01); *C08J 2433/26* (2013.01); *Y10T 428/139* (2015.01); *Y10T 428/1352* (2015.01); *Y10T 428/1393* (2015.01)

(58) Field of Classification Search
CPC ........ A61L 29/08; A61L 29/085; A61L 29/14; A61L 29/042; A61L 29/06; B05D 3/067; Y10T 428/1352; Y10T 428/139; Y10T 428/1393; C08J 3/28; C08J 7/12; C08J 7/18; C08F 2/48; C08F 220/56; C08F 291/02; C08F 291/04
USPC .................................................. 427/2.28, 287
See application file for complete search history.

(56) References Cited

U.S. PATENT DOCUMENTS

| | | | |
|---|---|---|---|
| 5,154,727 A | 10/1992 | Dyer | |
| 5,340,879 A | 8/1994 | Audenaert et al. | |
| 5,453,467 A | 9/1995 | Bamford et al. | |
| 5,637,460 A | 6/1997 | Swan et al. | |
| 5,688,252 A * | 11/1997 | Matsuda ............. A61M 5/2448 | |
| | | | 604/218 |
| 5,855,623 A | 1/1999 | English et al. | |
| 5,885,566 A | 3/1999 | Goldberg | |
| 5,889,073 A | 3/1999 | Zhang et al. | |
| 5,967,714 A | 10/1999 | Ottersbach et al. | |
| 6,001,894 A * | 12/1999 | Ottersbach ............. C08J 7/18 | |
| | | | 427/520 |
| 6,188,075 B1 | 2/2001 | Takayama et al. | |
| 6,203,856 B1 | 3/2001 | Ottersbach et al. | |
| 6,228,172 B1 | 5/2001 | Taylor et al. | |
| 6,358,557 B1 | 3/2002 | Wang et al. | |
| 6,808,738 B2 | 10/2004 | Ditizio et al. | |
| 7,348,055 B2 | 3/2008 | Chappa et al. | |
| 8,299,139 B1 | 10/2012 | Taranekar et al. | |
| 8,840,927 B2 | 9/2014 | Ditizio et al. | |
| 9,339,845 B2 * | 5/2016 | Minagawa ............. C08C 19/28 | |
| 9,469,736 B2 | 10/2016 | Minagawa | |
| 2002/0161065 A1 | 10/2002 | DiTizio et al. | |
| 2004/0086568 A1 | 5/2004 | Ditizio et al. | |
| 2004/0106732 A1 | 6/2004 | Tsuji et al. | |
| 2005/0137355 A1 | 6/2005 | Buckanin et al. | |
| 2006/0155057 A1 * | 7/2006 | Hermeling ............. A61L 15/60 | |
| | | | 525/50 |
| 2007/0003592 A1 | 1/2007 | Hissink | |
| 2007/0116971 A1 | 5/2007 | Yoshikawa et al. | |
| 2008/0016644 A1 | 1/2008 | Mizote et al. | |
| 2008/0103287 A1 * | 5/2008 | Chino .................... C08C 19/22 | |
| | | | 528/421 |
| 2008/0312377 A1 | 12/2008 | Schmidt et al. | |
| 2009/0169715 A1 | 7/2009 | Dias et al. | |
| 2009/0239089 A1 | 9/2009 | Agata et al. | |
| 2010/0255336 A1 | 10/2010 | Zabinski | |
| 2011/0160357 A1 | 6/2011 | Gerster et al. | |
| 2011/0274940 A1 | 11/2011 | Kyomoto et al. | |
| 2012/0021151 A1 | 1/2012 | Tatarka et al. | |
| 2012/0100369 A1 | 4/2012 | Hanazawa et al. | |
| 2013/0203883 A1 | 8/2013 | Minagawa | |
| 2013/0274367 A1 | 10/2013 | Minagawa et al. | |
| 2013/0310772 A1 | 11/2013 | Minagawa | |
| 2014/0039084 A1 | 2/2014 | Minagawa | |
| 2014/0128493 A1 | 5/2014 | Minagawa | |
| 2015/0203612 A1 | 7/2015 | Minagawa | |

FOREIGN PATENT DOCUMENTS

| | | |
|---|---|---|
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-179055 A | 7/1993 |
| JP | 6-25450 A | 2/1994 |
| JP | 6-510322 A | 11/1994 |
| JP | 7-100744 B2 | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-516736 A | 6/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |

(56) References Cited

FOREIGN PATENT DOCUMENTS

| JP | 2011-042755 A | 3/2011 |
|---|---|---|
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | 2012-162646 A | 8/2012 |
| JP | 2013-159629 A | 8/2013 |
| JP | 2013-208777 A | 10/2013 |
| JP | 2013-237801 A | 11/2013 |
| JP | 2013-237802 A | 11/2013 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2010/058848 A1 | 5/2010 |
| WO | WO 2010/131652 A1 | 11/2010 |
| WO | WO 2011/038483 | 4/2011 |
| WO | WO 2012/091169 A1 | 7/2012 |
| WO | WO 2012/165525 A1 | 12/2012 |

OTHER PUBLICATIONS

International Search Report and English translation thereof, dated Jan. 21, 2014, for International Application No. PCT/JP2013/081090.

International Search Report, dated Dec. 3, 2013, for International Application No. PCT/JP2013/074219.

International Search Report, dated Jul. 24, 2012, for International Application No. PCT/JP2012/064030.

U.S. Non-Final Office Action, dated May 8, 2015, for U.S. Appl. No. 13/756,837.

U.S. Non-Final Office Action, dated Oct. 20, 2014, for U.S. Appl. No. 13/756,837.

U.S. Notice of Allowance, dated Dec. 26, 2014, for U.S. Appl. No. 13/956,974.

U.S. Office Action (Requirement for Restriction/Election), dated May 9, 2014, for U.S. Appl. No. 13/956,974.

U.S. Office Action, dated Apr. 17, 2015, for U.S. Appl. No. 13/775,451.

U.S. Office Action, dated Aug. 25, 2014, for U.S. Appl. No. 13/956,974.

U.S. Office Action, dated Jun. 24, 2015, for U.S. Appl. No. 14/118,136.

U.S. Office Action, dated Sep. 21, 2015, for U.S. Appl. No. 14/107,746.

International Search Report and Written Opinion of the International Searching Authority, dated Jan. 20, 2015, for International Application No. PCT/JP2014/079947.

International Search Report, dated Aug. 19, 2014, for International Application No. PCT/JP2014/063268.

International Search Report, dated Feb. 25, 2014, for International Application No. PCT/JP2013/082409.

Jinan Haohua Industry Co., Ltd., "Ethanaminium, N,N,N-trimethyl-2-[(2-methyl-1-oxo-2-propen-1-yl) oxy]-, chloride (1:1)," CAS: 5039-78-1, Product Information Inquiry Description, found online on Dec. 27, 2016, http://guide7932.guidechem.com/pro-show2436647.html, pp. 1-2 (3 pages total).

U.S. Office Action, dated Nov. 3, 2016, for U.S. Appl. No. 14/896,096.

\* cited by examiner

SURFACE-MODIFIED ELASTIC BODY

TECHNICAL FIELD

The present invention relates to surface-modified elastic bodies, such as a gasket for syringes, a tire, a catheter, and a low protein adsorption material, each obtained by a predetermined surface modification method.

BACKGROUND ART

With a high regard for sealing properties, elastic bodies (e.g. rubber) are used for parts that slide while maintaining the sealing performance, e.g., a gasket which is integrated with a plunger of a syringe and forms a seal between the plunger and the barrel. Such elastic bodies, however, have a slight problem in their sliding properties (see Patent Literature 1). Thus, a sliding property improving agent (e.g. silicone oil) is applied to the sliding surface. It is, however, pointed out that silicone oil can accelerate adsorption and aggregation of proteins in recently marketed bio-preparations. Meanwhile, gaskets which are not coated with a sliding property improving agent have poor sliding properties, and thus do not allow plungers to be smoothly pushed but cause them to pulsate during administration. Hence, some problems occur such as an inaccurate injection amount and infliction of pain on patients.

A technique of coating with a self-lubricating PTFE film (see Patent Literature 2) is known to simultaneously satisfy such conflicting requirements, that is, the sealing properties and the sliding properties. The film, however, is generally expensive and thus increases the production cost of processed products, limiting its application range. Moreover, reliability concerns exist with the use of PTFE film coated products in applications where durability against repeated sliding motion is required. Another problem is that as PTFE is vulnerable to radiation, PTFE coated products cannot be sterilized by radiation.

Furthermore, the use in other applications where sliding properties in the presence of water are required can be considered. Specifically, water can be delivered without a loss by reducing the fluid resistance of the inner surface of a pre-filled syringe or the inner surface of a pipe or tube for delivering water, or by increasing or greatly reducing the contact angle with water. Another example is catheters which are inserted into blood vessels or urethras and are thus required to have high sliding properties so as to avoid hurting blood vessels or urethras and also avoid causing pain to patients. Moreover, drainage of water on wet roads and of snow on snowy roads can be improved by reducing the fluid resistance of the groove surfaces of tires, or by increasing or greatly reducing the contact angle with water. This leads to improved hydroplaning performance and enhanced grip performance, and therefore better safety. In addition, less adhesion of wastes and dusts can be expected when the sliding resistance of the sidewall surfaces of tires or walls of buildings is reduced, or when their contact angle with water is increased.

Further advantageous effects can be expected, such as: less pressure loss when water, an aqueous solution or the like is delivered through a diaphragm such as a diaphragm pump or valve; easy sliding of skis or snowboards, achieved by enhancing the sliding properties of the sliding surfaces thereof; better noticeability of road signs or signboards, achieved by enhancing the sliding properties thereof to allow snow to slide easily on the surface; reduction in water resistance or drag and in protein adsorption on the outer peripheries of ships, and therefore less adhesion of bacteria on the outer peripheries, achieved by reducing the sliding resistance of the outer peripheries or by increasing the contact angle with water; and reduction in water resistance or drag of swimsuits, achieved by improving the sliding properties of the thread surfaces thereof.

CITATION LIST

Patent Literature

Patent Literature 1: JP 2004-298220 A
Patent Literature 2: JP 2010-142537 A

SUMMARY OF INVENTION

Technical Problem

The present invention aims to solve the above problems and provide surface-modified elastic bodies, such as a gasket for syringes, a tire, a catheter, and a low protein adsorption material, each obtained by a surface modification method for modifying a rubber vulcanizate or a thermoplastic elastomer, the method being capable of providing surfaces with excellent properties such as excellent sliding properties, excellent durability against repeated sliding motion, and excellent performance in preventing adsorption and aggregation of proteins, and allowing the surfaces to maintain the sealing properties, without using expensive self-lubricating plastics.

Solution to Problem

The present invention relates to a gasket for syringes, at least partially having a surface modified by a surface modification method including:

step 1 of forming polymerization initiation points on a surface of an object to be modified that includes a rubber vulcanizate or a thermoplastic elastomer, and step 2 of radically polymerizing a monomer containing a C—N bond in a molecule thereof, starting from the polymerization initiation points, to grow polymer chains on the surface of the object to be modified.

The present invention relates to a tire, at least partially having a groove surface modified by a surface modification method including:

step 1 of forming polymerization initiation points on a surface of an object to be modified that includes a rubber vulcanizate or a thermoplastic elastomer, and step 2 of radically polymerizing a monomer containing a C—N bond in a molecule thereof, starting from the polymerization initiation points, to grow polymer chains on the surface of the object to be modified.

The present invention relates to a catheter, at least partially having a surface modified by a surface modification method including:

step 1 of forming polymerization initiation points on a surface of an object to be modified that includes a rubber vulcanizate or a thermoplastic elastomer, and step 2 of radically polymerizing a monomer containing a C—N bond in a molecule thereof, starting from the polymerization initiation points, to grow polymer chains on the surface of the object to be modified.

The present invention also relates to a low protein adsorption material, at least partially having a surface modified by a surface modification method including:

step 1 of forming polymerization initiation points on a surface of an object to be modified that includes a rubber vulcanizate or a thermoplastic elastomer, and step 2 of radically polymerizing a monomer containing a C—N bond in a molecule thereof, starting from the polymerization initiation points, to grow polymer chains on the surface of the object to be modified.

The rubber vulcanizate or thermoplastic elastomer preferably contains an allylic carbon atom which is a carbon atom adjacent to a double bond.

The polymerization initiation points are preferably formed by adsorbing a polymerization initiator on the surface of the object to be modified. Here, the polymerization initiator is preferably at least one of a benzophenone compound and a thioxanthone compound.

Preferably, the adsorbed polymerization initiator is further chemically bonded to the surface of the object to be modified by light irradiation.

The radical polymerization is preferably photo-radical polymerization. Here, the photo-radical polymerization preferably includes irradiation with light having a wavelength of 300 to 450 nm. Also, the radical polymerization preferably includes insertion of an inert gas into a reaction container and a reaction solution during or before light irradiation, to polymerize the monomer in an atmosphere replaced with the inert gas.

The monomer containing a C—N bond in a molecule thereof is preferably at least one selected from the group consisting of (meth)acrylamide, dimethyl(meth)acrylamide, diethyl(meth)acrylamide, isopropyl(meth)acrylamide, hydroxy(meth)acrylamide, and (meth)acryloyl morpholine.

The photo-radical polymerization preferably includes contacting the monomer containing a C—N bond in a molecule thereof or a solution of the monomer with the surface of the object to be modified or the surface of the object to be modified to which a polymerization initiator is adsorbed or covalently bonded, and then irradiating the surface with light to polymerize the monomer. Preferably, the monomer containing a C—N bond in a molecule thereof or the solution of the monomer includes a polymerization inhibitor and the monomer is polymerized in the presence of the polymerization inhibitor. The polymerization inhibitor is preferably 4-methylphenol.

Preferably, the polymer chains each have a length of 10 to 50000 nm.

ADVANTAGEOUS EFFECTS OF INVENTION

The present invention provides surface-modified elastic bodies, such as a gasket for syringes, a tire, a catheter, and a low protein adsorption material, each of which at least partially has a surface modified by a surface modification method including: step 1 of forming polymerization initiation points on a surface of an object to be modified that includes a rubber vulcanizate or a thermoplastic elastomer, and step 2 of radically polymerizing a monomer containing a C—N bond in a molecule thereof, starting from the polymerization initiation points, to grow polymer chains on the surface of the object to be modified. Thus, the surface of the object to be modified can have excellent sliding properties and excellent durability against repeated sliding motion, as well as favorable sealing properties. Since the obtained surface-modified elastic bodies have no PTFE polymer backbone, they can be sterilized by radiation such as gamma rays.

Moreover, the use of the monomer containing a C—N bond in a molecule thereof reduces adsorption of proteins, and thus enables prevention of adsorption and aggregation of proteins in bio-preparations.

DESCRIPTION OF EMBODIMENTS

The present invention relates to a surface modification method including: step 1 of forming polymerization initiation points on a surface of an object to be modified that includes a rubber vulcanizate or a thermoplastic elastomer, and step 2 of radically polymerizing a monomer containing a C—N bond in a molecule thereof, starting from the polymerization initiation points, to grow polymer chains on the surface of the object to be modified. The present invention also relates to surface-modified elastic bodies, such as a gasket for syringes, a tire, a catheter, and a low protein adsorption material, each of which at least partially has a surface modified by the surface modification method.

In step 1, polymerization initiation points are formed on a surface of a molded rubber vulcanizate or a molded thermoplastic elastomer (object to be modified).

The rubber vulcanizate or thermoplastic elastomer may suitably be one containing a carbon atom adjacent to a double bond (allylic carbon atom).

Examples of the rubber for the object to be modified include diene rubbers such as styrene-butadiene rubber, butadiene rubber, isoprene rubber, natural rubber, and deproteinized natural rubber; and butyl rubber and halogenated butyl rubber which have a degree of unsaturation of a few percent of isoprene units. In the case of the butyl rubber or halogenated butyl rubber, rubber crosslinked by triazine is preferred because the amount of matter extracted from the rubber vulcanizate is small. In this case, the rubber may contain an acid acceptor, and examples of suitable acid acceptors include hydrotalcites and magnesium carbonate.

Sulfur vulcanization is preferred for other rubbers. In this case, compounding agents commonly used for sulfur vulcanization may be added, such as vulcanization accelerators, zinc oxide, fillers, and silane coupling agents. Preferred examples of fillers include carbon black, silica, clay, talc, and calcium carbonate.

The vulcanization conditions for rubber may be appropriately set. The vulcanization temperature for rubber is preferably 150° C. or higher, more preferably 170° C. or higher, and further preferably 175° C. or higher.

Examples of the thermoplastic elastomer include polymer compounds having rubber elasticity at ordinary temperature owing to the aggregates of plastic components (hard segments) that serve as crosslinking points (e.g. thermoplastic elastomers (TPE) such as styrene-butadiene-styrene copolymers); and polymer compounds having rubber elasticity, obtained by mixing a thermoplastic component and a rubber component and dynamically crosslinking the mixture by a crosslinking agent (e.g. thermoplastic elastomers (TPV) such as polymer alloys containing a styrene block copolymer or olefinic resin together with a crosslinked rubber component).

Other suitable examples of the thermoplastic elastomer include nylon, polyester, polyurethane, polypropylene, and dynamically crosslinked thermoplastic elastomers thereof. In the case of using dynamically crosslinked thermoplastic elastomers, preferred examples thereof include those obtained by dynamically crosslinking halogenated butyl rubber in a thermoplastic elastomer. Here, the thermoplastic elastomer may preferably be nylon, polyurethane, polypropylene, or SIBS (styrene-isobutylene-styrene block copolymer), for example.

Polymerization initiation points can be formed, for example, by adsorbing a polymerization initiator on the surface of the object to be modified. Examples of the polymerization initiator include carbonyl compounds, organic sulfur compounds (e.g. tetraethylthiuram disulfide), persulfides, redox compounds, azo compounds, diazo compounds, halogen compounds, and photoreductive pigments. Preferred among these are carbonyl compounds.

The carbonyl compound as the polymerization initiator is preferably benzophenone or its derivative, and suitable examples thereof include benzophenone compounds represented by the following formula:

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary, secondary or tertiary amino group, a mercapto group, or a hydrocarbon group that may contain an oxygen atom, a nitrogen atom, or a sulfur atom; and any two adjacent groups thereof may be joined to each other to form a cyclic structure together with the carbon atoms to which they are bonded.

Specific examples of the benzophenone compounds include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because they contribute to favorable polymer brushes. The benzophenone compounds suitably include fluorobenzophenone compounds, and examples thereof include 2,3,4,5,6-pentafluorobenzophenone and decafluorobenzophenone.

Thioxanthone compounds can also be suitably used as the polymerization initiator because they can achieve a high polymerization rate, and can easily be adsorbed on and/or reacted with rubber or the like. For example, compounds represented by the following formula can be suitably used, wherein $R^{11}$ to $R^{14}$ and $R^{11'}$ to $R^{14'}$ are the same as or different from one another and each represent a hydrogen atom, a halogen atom, an alkyl group, a cyclic alkyl group, an aryl group, an alkenyl group, an alkoxy group, or an aryloxy group.

Examples of the thioxanthone compounds represented by the above formula include thioxanthone, 2-isopropylthioxanthone, 4-isopropylthioxanthone, 2,3-dimethylthioxanthone, 2,4-dimethylthioxanthone-2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are the compounds in which one or two, particularly two of $R^{11}$ to $R^{14}$ and $R^{11'}$ to $R^{14'}$ are alkyl substituents, and more preferred is 2,4-diethylthioxanthone.

The adsorption of a polymerization initiator (e.g. benzophenone compounds, thioxanthone compounds) on the surface of the object to be modified may be carried out according to a known method. In the case of using a benzophenone compound or a thioxanthone compound, for example, the benzophenone compound or thioxanthone compound is dissolved in an organic solvent to prepare a solution; a surface portion of the object to be modified is treated with this solution so that the compound is adsorbed on the surface portion; and, if necessary, the organic solvent is dried to be evaporated off, whereby polymerization initiation points are formed. The surface-treating method is not particularly limited as long as the solution of the benzophenone compound or thioxanthone compound can be brought into contact with the surface of the object to be modified. Suitable examples of the method include application of the benzophenone or thioxanthone compound solution, spraying thereof, and immersion of the surface into the solution. If only a part of the surface needs to be modified, it is sufficient to adsorb the polymerization initiator only onto a necessary part of the surface. In this case, for example, application of the solution or spraying of the solution is suitable. Examples of the solvent include methanol, ethanol, acetone, benzene, toluene, methyl ethyl ketone, ethyl acetate, and THF. Acetone is preferred because it does not swell the object to be modified and it is rapidly dried and evaporated off.

Preferably, after the target region to be modified is surface-treated with the benzophenone or thioxanthone compound solution so that the polymerization initiator is adsorbed, the polymerization initiator is further chemically bonded to the surface of the object to be modified by light irradiation. For example, the benzophenone or thioxanthone compound solution can be fixed on the surface by irradiation with ultraviolet light having a wavelength of 300 to 450 nm (preferably 300 to 400 nm, more preferably 350 to 400 nm). During step 1 and the fixing, hydrogen is abstracted from the rubber surface, and a carbon atom on the rubber surface is then covalently bonded to the carbon atom in C=O of benzophenone while the abstracted hydrogen is bonded to the oxygen atom in C=O, to form C—O—H. Moreover, since the hydrogen abstraction reaction selectively occurs on allylic hydrogen atoms in the object to be modified, the rubber preferably contains a butadiene or isoprene unit that contains an allylic hydrogen atom.

R: Hydrogen or C1-C4 Alkyl Group

In particular, preferably, the surface of the object to be modified is treated with a polymerization initiator to adsorb the polymerization initiator on the surface, and then the treated surface is irradiated with LED light having a wavelength of 300 to 400 nm to form polymerization initiation points. Especially preferably, the surface of the object to be modified is surface-treated with, for example, the benzophenone or thioxanthone compound solution to adsorb the polymerization initiator on the surface, and then the treated surface is irradiated with LED light having a wavelength of 300 to 400 nm so that the adsorbed polymerization initiator is chemically bonded to the surface. The LED light suitably has a wavelength of 355 to 380 nm.

In step 2, a monomer containing a C—N bond in a molecule (one molecule) thereof is radically polymerized starting from the polymerization initiation points formed in step 1, to grow polymer chains on the surface of the object to be modified. Consequently, a surface-modified elastic body (e.g. a gasket for syringes) is prepared in which the surface of the object to be modified is provided with polymer chains formed by radical polymerization of the monomer containing a C—N bond in a molecule thereof.

Suitable examples of the monomer containing a C—N bond in a molecule thereof include (meth)acrylamide; N-alkyl substituted (meth)acrylamide derivatives (e.g. N-ethyl(meth)acrylamide, N-n-propyl(meth)acrylamide, N-isopropyl(meth)acrylamide, N-cyclopropyl(meth)acrylamide, N-ethoxyethyl(meth)acrylamide); N,N-dialkyl substituted (meth)acrylamide derivatives (e.g. N,N-dimethyl(meth)acrylamide, N,N-ethylmethyl(meth)acrylamide, N,N-diethyl(meth)acrylamide); hydroxy(meth)acrylamide; hydroxy(meth)acrylamide derivatives (e.g. N-hydroxyethyl(meth)acrylamide); and cyclic group-containing (meth)acrylamide derivatives (e.g. (meth)acryloyl morpholine). Preferred among these are (meth)acrylamide, dimethyl(meth)acrylamide, diethyl(meth)acrylamide, isopropyl(meth)acrylamide, hydroxy(meth)acrylamide, and (meth)acryloyl morpholine, and more preferred is (meth)acrylamide, particularly acrylamide, in terms of low protein adsorption properties.

The following describes an example of the method for radically polymerizing a monomer containing a C—N bond in a molecule thereof in step 2. First, a (liquid) monomer containing a C—N bond or a solution thereof is applied (sprayed) to the surface of the object to be modified to which a benzophenone compound, a thioxanthone compound or the like is adsorbed or covalently bonded, or alternatively the object to be modified is immersed in a (liquid) monomer containing a C—N bond or a solution thereof. Then, the object to be modified is irradiated with light (e.g. ultraviolet light) to allow radical polymerization (photo-radical polymerization) of the monomer to proceed, thereby growing polymer chains on the surface of the object to be modified. Additionally, after the application of the monomer or a solution thereof, the surface of the object to be modified may be covered with a sheet of transparent glass, PET, polycarbonate or the like, followed by irradiation of the covered surface with light (e.g. ultraviolet light) to allow radical polymerization (photo-radical polymerization) of the monomer to proceed, thereby growing polymer chains on the surface of the object to be modified.

Conventionally known materials and methods may be employed for the solvent for application (spraying), the method for application (spraying), the method for immersion, the conditions for irradiation, and the like. The solution of the monomer containing a C—N bond (radically polymerizable monomer) may be an aqueous solution or a solution prepared by dissolving the monomer in an organic solvent that does not dissolve a polymerization initiator (e.g. benzophenone compounds) to be used. Furthermore, the (liquid) monomer containing a C—N bond or a solution thereof may be in admixture with a known polymerization inhibitor such as 4-methylphenol.

In the present invention, radical polymerization of the monomer containing a C—N bond is allowed to proceed by light irradiation after the (liquid) monomer or a solution thereof is applied to the surface, or after the surface is immersed in the (liquid) monomer or a solution thereof. UV irradiation sources with an emission wavelength mainly in the ultraviolet region may suitably be used, such as high-pressure mercury lamps, metal halide lamps, and LED lamps. The light dose may be appropriately adjusted in consideration of the polymerization time and uniform progress of the reaction. In order to prevent polymerization inhibition due to active gas like oxygen in a reaction container, oxygen is preferably removed from the reaction container and the reaction solution during or before the light irradiation. Thus, some methods may appropriately be employed, for example, in which an inert gas like nitrogen gas or argon gas is inserted into the reaction container and the reaction solution to discharge active gas like oxygen from the reaction system so as to replace the atmosphere in the reaction system with the inert gas. Moreover, in order to prevent reaction inhibition due to oxygen or the like, some measures may be appropriately taken, for example, in which a UV irradiation source is placed such that no air layer (oxygen content: 15% or higher) exists between the reaction container made of glass, plastics or the like and the reaction solution or the object to be modified.

For irradiation with ultraviolet light, the ultraviolet light preferably has a wavelength of 300 to 450 nm, more preferably a wavelength of 300 to 400 nm. Such ultraviolet light enables polymer chains to be favorably formed on the surface of the object to be modified. Ultraviolet light having a wavelength below 300 nm unfortunately polymerizes the monomer alone, not starting from the surface, to form free polymers. The preferred examples of the light source include high pressure mercury lamps, LEDs with a center wavelength of 365 nm, and LEDs with a center wavelength of 375 nm. In particular, irradiation with LED light having a wavelength of 300 to 400 nm is preferred, and irradiation with LED light having a wavelength of 355 to 380 nm is more preferred. For example, LEDs with a center wavelength of 365 nm, which is close to the excitation wavelength (366 nm) of benzophenone, are particularly preferred in terms of efficiency.

Polymer chains formed in step 2 provide excellent sliding properties, excellent durability, and excellent performance in preventing adsorption and aggregation of proteins, and also allow the surface to maintain good sealing properties. The polymerization degree of the formed polymer chains is preferably 20 to 200000, and more preferably 350 to 50000. If the polymerization degree is less than 20, the polymer chains tend to be so short that they may be concealed by irregularities on the surface of the object to be modified, and therefore tend to fail to impart sliding properties to the surface. If the polymerization degree exceeds 200000, the amount of the monomer used is increased, which tends to lead to an economic disadvantage.

The polymer chains formed in step 2 preferably each have a length of 10 to 50000 nm, more preferably 100 to 50000 nm. Polymer chains shorter than 10 nm are unlikely to provide good sliding properties. Polymer chains longer than 50000 nm are unlikely to provide better sliding properties, while they are likely to drive up the cost of raw materials due to the expensive monomer. In addition, in such cases, surface patterns formed by the surface treatment are likely to be visible to the naked eye, which tends to spoil the appearance and to decrease the sealing properties.

In step 2, two or more species of monomers containing a C—N bond in a molecule thereof may be radically polymerized simultaneously, starting from the polymerization initiation points. Moreover, multiple kinds of polymer chains may be grown on the surface of the object to be modified. The surface modification method may include crosslinking between the polymer chains. In this case, ionic crosslinking or crosslinking via a hydrophilic group containing an oxygen atom may be formed between the polymer chains. Moreover, a small amount of a compound having two or more vinyl groups per molecule thereof may be added prior to the polymerization, to introduce crosslinks between the polymer chains during the polymerization. Preferred examples of the compound having two or more vinyl groups per molecule thereof include N,N'-methylenebisacrylamide.

Treatment of a rubber vulcanizate or a thermoplastic elastomer by the surface modification method enables to provide a surface-modified elastic body. For example, a surface-modified elastic body excellent in sliding properties in the presence of water or in a dry state can be obtained. This surface-modified elastic body is excellent in that it has low friction and low water resistance or drag. Moreover, treatment of at least part of a three-dimensional solid (e.g. elastic body) by the above method enables to provide a surface-modified elastic body having better quality. Preferred examples of such a surface-modified elastic body include polymer brushes. The polymer brush herein means an assembly of graft polymer chains obtained by the "grafting from" approach by surface-initiated living radical polymerization. The graft chains are preferably oriented in a direction substantially vertical to the surface of the object to be modified because, in such a case, the entropy is reduced and thus the molecular mobility of the graft chains is reduced, which ensures sliding properties. Preferred are semidilute brushes and concentrated brushes which have a brush density of 0.01 chains/nm$^2$ or higher.

Furthermore, treatment of a rubber vulcanizate or a thermoplastic elastomer by the surface modification method enables to produce a gasket for syringes which at least partially has a modified surface. The modification is preferably performed at least on the sliding portion of the gasket surface, or may be performed on the entire surface.

Figure 1:
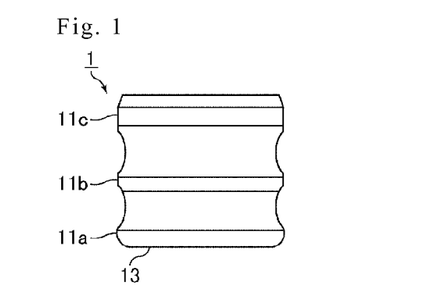
FIG. 1 is an exemplary side view of an embodiment of a gasket for syringes.

FIG. 1 is an exemplary side view of an embodiment of a gasket for syringes. A gasket 1 shown in FIG. 1 has three circular protruding portions 11a, 11b and 11c each of which continuously protrudes along the circumferential direction on the outer periphery that is to be in contact with the inner periphery of a syringe barrel. Examples of the portion of the gasket 1 to which the surface modification is applied include: (1) the surfaces of protruding portions to be in contact with a syringe barrel, such as the circular protruding portions 11a, 11b and 11c; (2) the entire side surface including the circular protruding portions 11a, 11b and 11c; and (3) the entire side surface and a bottom surface 13.

Furthermore, when grooves in the tread of a tire for use on vehicles such as passenger cars are treated by the surface modification method to form a polymer brush on the grooves, the fluid resistance of the groove surface on wet or snowy roads is reduced, and the contact angle with water is increased. Thus, the abilities to remove and drain water or snow are enhanced so that the grip performance can be improved.

Figure 2:
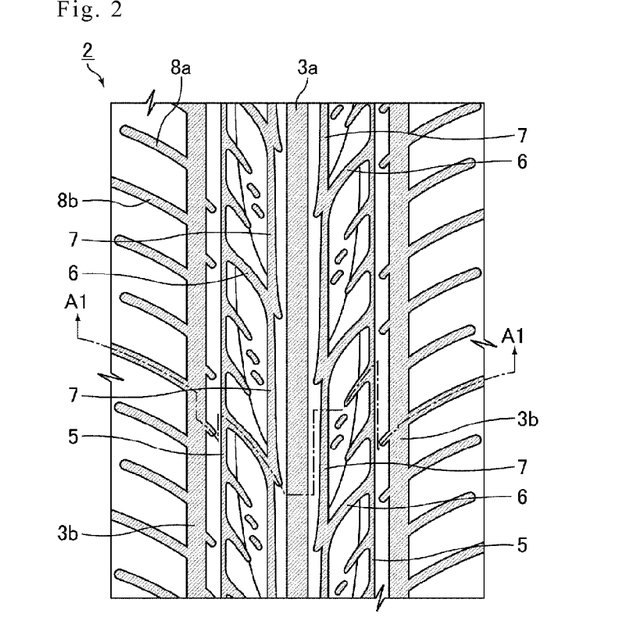
FIG. 2 is an exemplary development view of a tread portion of a pneumatic tire (the whole tire is not illustrated).
Figure 3:
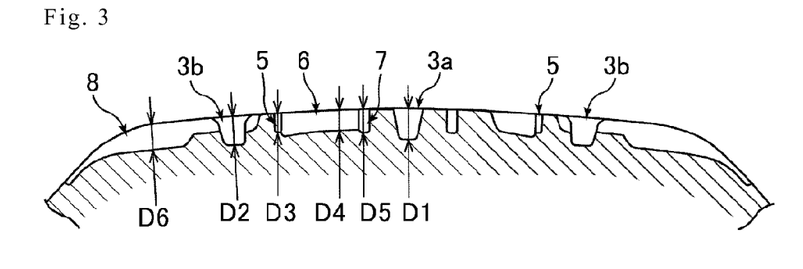
FIG. 3 is an exemplary A1-A1 cross-sectional view of FIG. 2.

FIG. 2 is an exemplary development view of a tread portion 2 of a pneumatic tire (the whole tire is not illustrated). FIG. 3 is an exemplary A1-A1 cross-sectional view of FIG. 2.

In FIGS. 2 and 3, a longitudinal center groove 3a (groove depth D1) and longitudinal shoulder grooves 3b (groove depth D2) are straight grooves straightforwardly extending in the circumferential direction of the tire. Such straight grooves can contribute to low drainage resistance and high drainage performance during straight travelling.

The pneumatic tire also has fine grooves 5 (groove depth D3) extending in the tire circumferential direction on the side of the longitudinal shoulder groove 3b; beveled intermediate grooves 6 (groove depth D4) extending with an inclination from the fine groove 5 toward the longitudinal center groove 3a; connecting grooves 7 (groove depth D5) located at positions inner than the fine grooves 5 in the axis direction of the tire and connecting the beveled intermediate grooves 6 next to one another in the circumferential direction of the tire; and lateral shoulder grooves 8, 8a and 8b (groove depth D6) extending from the longitudinal shoulder groove 3b toward the outside of the tire; and the like, and these grooves can also contribute to drainage performance. Treatment of these grooves by the above method enables to achieve the aforementioned effects.

EXAMPLES

The following will describe the present invention in more detail, referring to, though not limited to, examples.

Example 1

A chlorobutyl rubber (degree of unsaturation: 1 to 2%) having isoprene units was crosslinked by triazine to prepare a vulcanized rubber gasket (vulcanized at 180° C. for 10 minutes). The vulcanized rubber gasket was immersed in a 1 wt % solution of benzophenone in acetone so that benzophenone was adsorbed to the surface of the rubber vulcanizate. Then, the rubber vulcanizate was taken out and dried.

The dried rubber vulcanizate was immersed in an aqueous acrylamide solution (2.5 M) in a glass reaction container, and was irradiated with ultraviolet light using an LED-UV lamp (2 mW/cm$^2$) with a wavelength of 365 nm for 60 hours to cause radical polymerization, whereby polymer chains were grown on the rubber surface. In this manner, a surface-modified elastic gasket (polymer brush) was obtained.

Example 2

A surface-modified elastic gasket was prepared in the same manner as in Example 1, except that the aqueous acrylamide solution (2.5 M) was changed to an aqueous acrylamide solution (1.25 M), and the ultraviolet light irradiation was performed for 120 hours.

Example 3

A surface-modified elastic gasket was prepared in the same manner as in Example 1, except that the 1 wt % solution of benzophenone in acetone was changed to a 1 wt % solution of 2,4-dimethylthioxanthone in acetone, and the ultraviolet light irradiation was performed for 30 minutes.

Comparative Example 1

A vulcanized rubber gasket (vulcanized at 180° C. for 10 minutes) prepared by crosslinking chlorobutyl rubber by triazine was used.

Example 4

A chlorobutyl rubber (degree of unsaturation: 1 to 2%) having isoprene units was crosslinked by triazine to prepare a vulcanized rubber sheet (thickness: 2 mm, vulcanized at 180° C. for 10 minutes). The vulcanized rubber sheet was immersed in a 1 wt % solution of benzophenone in acetone so that benzophenone was adsorbed to the surface of the rubber vulcanizate. Then, the rubber vulcanizate was taken out and dried.

The dried rubber vulcanizate was immersed in an aqueous acrylamide solution (2.5 M) in a glass reaction container, and was irradiated with ultraviolet light using an LED-UV lamp (2 mW/cm$^2$) with a wavelength of 365 nm for 60 hours to cause radical polymerization, whereby polymer chains were grown on the rubber surface. In this manner, a surface-modified elastic sheet (polymer brush) was obtained.

Surface-modified elastic bodies prepared in the examples and comparative example were evaluated by the following methods.

(Length of Polymer Chains)

The length of polymer chains formed on the surface of the rubber vulcanizate was measured on a cross section of the modified rubber vulcanizate with polymer chains formed thereon, using an SEM at an accelerating voltage of 15 kV and a magnification of 1000 times. The thickness of the polymer layer measured on photographs was regarded as the length of the polymer chains.

(Friction Resistance)

The friction resistance of the surface of the surface-modified elastic body was measured as follows. The vulcanized rubber gasket prepared in each of the examples and comparative example was inserted into a COP resin barrel of a syringe and further pressed (pressing rate: 100 mm/min) into the barrel using a tensile tester while the friction resistance was measured. Based on the equation shown below, the friction resistance of each gasket prepared in the examples and comparative example was expressed as a friction resistance index relative to the friction resistance of Comparative Example 1 regarded as 100. A smaller index indicates a lower friction resistance.

(Friction resistance index)=(Friction resistance of each example)/(Friction resistance of Comparative Example 1)×100

(Protein Adsorption Test)

The surface-modified elastic sheet was contacted with a bovine serum albumin solution (1 mg/mL) at 37° C. for three hours. The adsorbed bovine serum albumin (protein) was then extracted in accordance with JIS T9010, and the amount of the protein in the extract was determined by Lowry method. The obtained value was converted to a value per area of the surface-modified elastic sheet.

TABLE 1

|  | Example | | | Comparative Example |
|---|---|---|---|---|
|  | 1 | 2 | 3 | 1 |
| Entire length of polymer chains (nm) | 12000 | 9000 | 14000 | — |
| Friction resistance index | 1.75 | 2.15 | 1.55 | 100 |

TABLE 2

|  | Example 4 |
|---|---|
| Protein adsorption amount (µg/cm$^2$) | 0.3 |

Table 1 demonstrates that the surfaces of the surface-modified elastic bodies prepared in the examples had greatly reduced friction resistance and therefore good sliding properties. Moreover, as only the surfaces were modified, they had sealing properties similar to that in Comparative Example 1.

A protein adsorption amount exceeding 0.4 µg/cm$^2$ tends to lead to a stack of denatured protein strongly adsorbed on the surface. Table 2 demonstrates that the protein adsorption amount in Example 4 was 0.3 µg/cm$^2$, which is sufficiently small, causing no problem.

Thus, in the case where the present invention is applied to a gasket for a plunger of a syringe, sufficient sealing properties are achieved while the friction of the plunger with the syringe barrel is reduced. Consequently, operations using such a syringe can be easily and accurately performed. Moreover, in the case where a syringe barrel is formed from a thermoplastic elastomer, and polymer chains are formed on its inner surface, operations using such a syringe can be easily performed as mentioned above. Furthermore, the present invention allows only a small amount of proteins to adsorb to the surface, and thus can prevent adsorption and aggregation of proteins in bio-preparations.

Additionally, the effects mentioned earlier can be expected when polymer chains are formed on the surfaces of grooves in treads and sidewalls of tires for vehicles such as passenger cars, on the surfaces of diaphragms, on the sliding surfaces of skis and snowboards, and on the surfaces of swimsuits, road signs, sign boards, and the like.

REFERENCE SIGNS LIST

1: gasket
11a, 11b, 11c: circular protruding portion
13: bottom surface
2: tread portion
3a: longitudinal center groove
3b: longitudinal shoulder groove
5: fine groove
6: beveled intermediate groove
7: connecting groove
8, 8a, 8b: lateral shoulder groove

The invention claimed is:

1. A gasket for syringes which comprises a halogenated butyl rubber, wherein the gasket has a surface at least partially modified by a surface modification method comprising:
   step 1 of forming polymerization initiation points on the gasket surface, and
   step 2 of radically polymerizing a monomer containing a C—N bond in a molecule thereof, starting at the polymerization initiation points, so as to grow polymer chains on the gasket surface.

2. A low protein adsorption material which comprises a halogenated butyl rubber, wherein the low protein adsorption material has a surface at least partially modified by a surface modification method comprising:
   step 1 of forming polymerization initiation points on the low protein adsorption material surface, and
   step 2 of radically polymerizing a monomer containing a C—N bond in a molecule thereof, starting at the polymerization initiation points, so as to grow polymer chains on the low protein adsorption material surface.

3. The low protein adsorption material according to claim 2, wherein the polymerization initiation points are formed by adsorbing a polymerization initiator on the low protein adsorption material surface.

4. The low protein adsorption material according to claim 3, wherein the polymerization initiator is at least one of a benzophenone compound and a thioxanthone compound.

5. The low protein adsorption material according to claim 3, wherein the adsorbed polymerization initiator is further chemically bonded to the low protein adsorption material surface by light irradiation.

6. The low protein adsorption material according to claim 2, wherein the radical polymerization is photo-radical polymerization.

7. The low protein adsorption material according to claim 6, wherein the photo-radical polymerization comprises irradiation with light having a wavelength of 300 to 450 nm.

8. The low protein adsorption material according to claim 2, wherein the radical polymerization comprises introduction of an inert gas into a reaction container containing the low protein adsorption material and exposure of the low protein adsorption material to light irradiation along with introduction of a reaction solution into the reaction container during or before light irradiation, so as to polymerize the monomer in an atmosphere of the inert gas.

9. The low protein adsorption material according to claim 2, wherein the monomer containing a C—N bond in a molecule thereof is at least one selected from the group consisting of (meth)acrylamide, dimethyl(meth)acrylamide, diethyl(meth)acrylamide, isopropyl(meth)acrylamide, hydroxy(meth)acrylamide, and (meth)acryloyl morpholine.

10. The low protein adsorption material according to claim 6, wherein the photo-radical polymerization comprises contacting the monomer containing a C—N bond in a molecule thereof or a solution of the monomer with the low protein adsorption material surface to which a polymerization initiator is adsorbed or covalently bonded, and then irradiating the low protein adsorption material surface with light to polymerize the monomer.

11. The low protein adsorption material according to claim 10, wherein the monomer containing a C—N bond in a molecule thereof or the solution of the monomer includes a polymerization inhibitor, and the monomer is polymerized in the presence of the polymerization inhibitor.

12. The low protein adsorption material according to claim 11, wherein the polymerization inhibitor is 4-methylphenol.

13. The low protein adsorption material according to claim 2, wherein the polymer chains each have a length of 10 to 50,000 nm.

* * * * *